(12) United States Patent
Dovichi et al.

(10) Patent No.: US 9,234,880 B2
(45) Date of Patent: Jan. 12, 2016

(54) SHEATH-FLOW ELECTROSPRAY INTERFACE

(75) Inventors: Norman Dovichi, South Bend, IN (US); Roza Wojcik, Lawrence, MI (US)

(73) Assignee: University of Washington through its Center for Commercialization, Seattle, WA (US)

( * ) Notice: Subject to any disclaimer, the term of this patent is extended or adjusted under 35 U.S.C. 154(b) by 312 days.

(21) Appl. No.: 13/488,073

(22) Filed: Jun. 4, 2012

(65) Prior Publication Data

US 2013/0140180 A1 Jun. 6, 2013

Related U.S. Application Data

(60) Provisional application No. 61/492,950, filed on Jun. 3, 2011.

(51) Int. Cl.
*G01N 30/72* (2006.01)
*G01N 27/447* (2006.01)
*H01J 49/16* (2006.01)

(52) U.S. Cl.
CPC ...... *G01N 30/7266* (2013.01); *G01N 27/44717* (2013.01); *G01N 27/44743* (2013.01); *H01J 49/167* (2013.01)

(58) Field of Classification Search
CPC ............ H01J 49/167; G01N 27/44717; G01N 27/44769; G01N 30/7266; G01N 30/463; G01N 30/465; G01N 30/726; G01N 30/7273; G01N 2030/6013
See application file for complete search history.

(56) References Cited

U.S. PATENT DOCUMENTS 5,423,964 A * 6/1995 Smith et al. ................... 204/452
2004/0113068 A1* 6/2004 Bousse et al. ................ 250/288

OTHER PUBLICATIONS

Liu et al., Rapid Commun. Mass Spectrom. 19, 187-192, 2005.*
Brenner-Weiss., J. Chromatography A, 1009, 2003, 147-153.*
Lewis, K.C., et al., "Comprehensive On-Line RPLC-CZE-MS of Peptides," Journal of the American Society for Mass Spectrometry 8(5):495-500, May 1997.
Zhang, B., et al., "Microfabricated Devices for Capillary Electrophoresis-Electrospray Mass Spectrometry," Analytical Chemistry 71(15):3258-3264, Aug. 1999.
Andren, P.E., et al., "Micro-Electrospray: Zeptomole/Attomole per Microliter Sensitivity for Peptides," Journal of the American Society for Mass Spectrometry 5(9):867-869, Sep. 1994.
Brown, J.R., and B.S. Hartley, "The Disulphide Bridges of Chymotrypsinogen-A," Proceedings of the Third International Meeting of the Biochemical Society, Biochemical Journal 89:59P-60P, 1963.
Cermak, N. (/u/cerman/), "sig Man," SourceForge.net, 2010, <http://sourceforge.net/projects/sigman/> [retrieved at least as early as May 24, 2010], 2 pages.

(Continued)

*Primary Examiner* — Luan Van
*Assistant Examiner* — Steven Rosenwald
(74) *Attorney, Agent, or Firm* — Christensen O'Connor Johnson Kindness PLLC

(57) ABSTRACT

A sheath-flow interface for producing electrospray from a capillary is provided. The electrospray generated by the interface can be used as the source of ions for mass spectrometry. In the interface, electrokinetic flow moves a sheath liquid past the end of a capillary so as to mix with an analyte effluent discharged from the capillary. The mixture of sheath liquid and analyte is directed to an electrospray emitter in order to generate an electrospray.

19 Claims, 6 Drawing Sheets

(56) References Cited

OTHER PUBLICATIONS

Chang, Y.Z., and G.R. Her, "Sheathless Capillary Electrophoresis/Electrospray Mass Spectrometry Using a Carbon-Coated Fused-Silica Capillary," Analytical Chemistry 72(3):626-630, Feb. 2000.

Cole, R.B., "Some Tenets Pertaining to Electrospray Ionization Mass Spectrometry," Journal of Mass Spectrometry 35(7):763-772, Jul. 2000.

Dose, E.V., and G.A. Guiochon, "Internal Standardization Technique for Capillary Zone Electrophoresis," Analytical Chemistry 63(11):1154-1158, Jun. 1991.

Emmett, M.R., and R.M. Caprioli, "Micro-Electrospray Mass Spectrometry: Ultra-High-Sensitivity Analysis of Peptides and Proteins," Journal of the American Society for Mass Spectrometry 5(7):605-613, Jul. 1994.

Figeys, D., et al., "Protein Identification by Capillary Zone Electrophoresis/Microelectrospray Ionization-Tandem Mass Spectrometry at the Subfemtomole Level," Analytical Chemistry 68(11):1822-1828, Jun. 1996.

Hsieh, F., et al., "A Novel Nanospray Capillary Zone Electrophoresis/Mass Spectrometry Interface," Rapid Communications in Mass Spectrometry 13(1):67-72, Jan. 1999.

Johnson, T., et al., "A CE-MALDI Interface Based on the Use of Prestructured Sample Supports," Analytical Chemistry 73(8):1670-1675, Apr. 2001.

Jorgenson, J.W., and K.D. Lukacs, "Zone Electrophoresis in Open-Tubular Glass-Capillaries," Analytical Chemistry 53(8):1298-1302, Jul. 1981.

Käll, L., et al., "Semi-Supervised Learning for Peptide Identification From Shotgun Proteomics Datasets," Nature Methods 4(11):923-925, Nov. 2007.

Kašička, V., "Recent Advances in CE and CEC of Peptides (2007-2009)," Electrophoresis 31(1):122-146, Jan. 2010.

Kirby, D.P., et al., "A CE/ESI-MS Interface for Stable, Low-Flow Operation," Analytical Chemistry 68(24):4451-4457, Dec. 1996.

Lee, E.D., et al "Liquid Junction Coupling for Capillary Zone Electrophoresis/Ion Spray Mass Spectrometry," Biomedical and Environmental Mass Spectrometry 18(9):844-850, Sep. 1989.

Liu, C.C., et al., "Design, Optimisation, and Evaluation of a Sheath Flow Interface for Automated Capillary Electrophoresis-Electrospray-Mass Spectrometry," Electrophoresis 26(7-8):1366-1375, Apr. 2005.

Maxwell, E.J., and D.D.Y. Chen, "Twenty Years of Interface Development for Capillary Electrophoresis-Electrospray Ionization-Mass Spectrometry," Analytica Chimica Acta 627(1):25-33, Oct. 2008.

Maziarz, E.P., III, et al., "Polyaniline: A Conductive Polymer Coating for Durable Nanospray Emitters," Journal of the American Society for Mass Spectrometry 11(7):659-663, Jul. 2000.

Mechref, Y., and M.V. Novotny, "Glycomic Analysis by Capillary Electrophoresis-Mass Spectrometry," Mass Spectrometry Reviews 28(2):207-222, Mar.-Apr. 2009.

Moini, M., "Simplifying CE-MS Operation. 2. Interfacing Low-Flow Separation Techniques to Mass Spectrometry Using a Porous Tip," Analytical Chemistry 79(11):4241-4246, Jun. 2007.

Moseley, M.A., et al., "Determination of Bioactive Peptides Using Capillary Zone Electrophoresis/Mass Spectrometry," Analytical Chemistry 63(2):109-114, Jan. 1991.

Nesbitt, C.A., et al., "Recent Applications of Capillary Electrophoresis-Mass Spectrometry (CE-MS): CE Performing Functions Beyond Separation," Analytica Chimica Acta 627(1):3-24, Oct. 2008.

Nilsson, S.L., et al., "A Chemometric Study of Active Parameters and Their Interaction Effects in a Nebulized Sheath-Liquid Electrospray Interface for Capillary Electrophoresis-Mass Spectrometry," Electrophoresis 25(13):2100-2107, Jul. 2004.

Olivares, J.A., et al., "On-Line Mass Spectrometric Detection for Capillary Zone Electrophoresis," Analytical Chemistry 59(8):1230-1232, Apr. 1987.

Pantůčková, P., et al., "Electrolyte Systems for On-Line CE-MS: Detection Requirements and Separation Possibilities," Electrophoresis 30(1):203-214, Jan. 2009.

Ramautar, R., et al., "CE-MS in Metabolomics," Electrophoresis 30(1):276-291, Jan. 2009.

Schoenherr, R.M., et al., "CE-Microreactor-CE-MS/MS for Protein Analysis," Analytical Chemistry 79(6):2230-2238, Mar. 2007.

Settlage, R.E., et al., "A Novel µ-ESI Source for Coupling Capillary Electrophoresis and Mass Spectrometry: Sequence Determination of Tumor Peptides at the Attomole Level," Journal of Microcolumn Separations 10(3):281-285, Dec. 1998.

Smith, R.D., et al., "Capillary Zone Electrophoresis-Mass Spectrometry Using an Electrospray Ionization Interface," Analytical Chemistry 60(5):436-441, Mar. 1988.

Song, E.J., et al., "CE at the Omics Level: Towards Systems Biology—An Update," Electrophoresis 29(1):129-142, Jan. 2008.

Vannatta, M.W., et al., "CE-MALDI Interface Based on Inkjet Technology," Electrophoresis 30(23):4071-4074, Dec. 2009. (Author manuscript PMCID: PMC2832290, available on PMC Dec. 1, 2010,11 pages.).

Wilm, M., and M. Mann, "Analytical Properties of the Nanoelectrospray Ion Source," Analytical Chemistry 68(1):1-8, Jan. 1996.

Wojcik, R., et al., "Automated Enzyme-Based Diagonal Capillary Electrophoresis: Application to Phosphopeptide Characterization," Analytical Chemistry 82(4):1564-1567, Feb. 2010. (Author manuscript PMCID: PMC2834226, available on PMC Feb. 15, 2011, 10 pages.).

Wojcik, R., et al., "Reaction of Fluorogenic Reagents With Proteins: I. Mass Spectrometric Characterization of the Reaction With 3-(2-furoyl)quinoline-2-carboxaldehyde, Chromeo P465, and Chromeo P503," Journal of Chromatography A 1194(2):243-248, Jun. 2008.

Wojcik, R., et al., "Simplified Capillary Electrophoresis Nanospray Sheath-Flow Interface for High Efficiency and Sensitive Peptide Analysis," Rapid Communications in Mass Spectrometry 24(17):2554-2560, Sep. 2010.

Zamfir, A.D., "Recent Advances in Sheathless Interfacing of Capillary Electrophoresis and Electrospray Ionization Mass Spectrometry," Journal of Chromatography A 1159(1-2):2-13, Aug. 2007.

Zhang, B., et al., "Proteomic Parsimony Through Bipartite Graph Analysis Improves Accuracy and Transparency," Journal of Proteome Research 6(9):3549-3557, Sep. 2007. (Author manuscript PMCID: PMC2810678, available on PMC Jan. 25, 2010, 16 pages.).

Zhong, X., et al., "Field Distribution in an Electrospray Ionization Source Determined by Finite Element Method," Rapid Communications in Mass Spectrometry 23(5):689-697, Mar. 2009.

* cited by examiner

SHEATH-FLOW ELECTROSPRAY INTERFACE

CROSS-REFERENCE TO RELATED APPLICATION

This application claims the benefit of U.S. Provisional Application No. 61/492,950, filed Jun. 3, 2011, the disclosure of which is expressly incorporated herein by reference in its entirety.

BACKGROUND

Hyphenation of capillary electrophoresis (CE) with electrospray ionization mass spectrometry (MS) was developed in the late 1980s and has steadily developed since. Capillary electrophoresis-electrospray ionization interfaces generally fall into three categories: sheathless, co-axial sheath low, and liquid junction interfaces.

Sheath flow interfaces use a coaxial sheath liquid that mixes with analytes as they migrate from the separation capillary. The purpose of the sheath liquid is to provide electrical contact between the electrophoretic separation and the electrospray ionization source. Sheath liquid can also modify separation buffer to make it more compatible with MS detection. The sheath-flow interface originally developed is now commercially available. In that design, the distal end of the separation capillary is inserted inside a concentric tube, with the capillary's end extending beyond the tube. Electrical contact is made by a sheath liquid flowing over the capillary protruding from the tube, and a nebulizer gas is supplied to assist the spray formation. The sheath liquid needs to be pumped to maintain a stable spray and the interface operates at relatively high sheath flow rates, typically in the range of several microliters per minute, which can result in significant sample dilution.

In a liquid junction interface, the separation capillary and electrospray emitter are separated by a small gap. Electrical contact is made with this gap to drive the electrospray. Unfortunately, the gap can contribute to a loss of separation efficiency.

Sheathless interface designs eliminate sample dilution associated with the sheath liquid, which tends to result in higher sensitivity. In sheathless interfaces, the separation capillary often serves as the electrospray emitter. Ongoing research in the design of a sheathless interface mainly focuses on establishing electrical contact at the distal end of the separation capillary. Variations include coating the outer tip of the capillary with metal, inserting an electrode inside the capillary outlet, use of porous etched capillary walls, and the use of a microdialysis junction. The major drawbacks of sheathless interfaces are spray instability due to the very low flow rates produced in some separation conditions, and the limited choices of separation buffers due to lack of post column chemistry.

To overcome some of the problems associated with both the original sheath flow and sheathless interface designs, a low flow version of a sheath flow interface was introduced. In this design, the separation capillary was inserted inside a tapered glass emitter. A second capillary was inserted inside the emitter, supplying sheath liquid, pumped at the rate of 1 µL/min. Electrospray voltage was supplied by a stainless steel wire inserted into the emitter.

Sheath flow interfaces with tapered emitters can operate in the nanospray regime, which is associated not only with supporting lower flow rates but also with better desolvation, enhanced sensitivity, and increased salt tolerance. However, attempting to produce a nanospray from CE effluent presents many technical issues that must be overcome in order to advance the field of CE-MS

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, a sheath-flow interface for producing electrospray from a capillary is provided. In one embodiment, the interface includes:

a capillary configured to contain an analyte liquid, the capillary having an injection end configured to receive the analyte liquid and a distal end configured to expel analyte effluent;

an electrospray emitter coaxially disposed surrounding at least the distal end of the capillary, the electrospray emitter having a distal end that is tapered to terminate at an opening, the opening being coaxially disposed in relation to the distal end of the capillary; and a sheath liquid reservoir in liquid communication with an interior of the electrospray emitter, such that an electrically conductive sheath liquid is allowed to flow from the sheath liquid reservoir, through a connecting fixture intermediate the capillary and the electrospray emitter, across the distal end of the capillary, and through the opening at the distal end of the electrospray emitter;

wherein the sheath liquid provides electrical contact between the capillary and the electrospray emitter;

wherein the sheath-flow interface is configured to produce a nanospray generated by electrokinetic flow of the sheath liquid mixed with the analyte effluent; and wherein the electrokinetic flow is generated by an electric potential between the electrospray emitter and a target surface disposed adjacent, but not in physical contact with the opening of the emitter.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

In one aspect, a sheath-flow interface for producing electrospray from a capillary is provided. In one embodiment, the interface includes:

a capillary configured to contain an analyte liquid, the capillary having an injection end configured to receive the analyte liquid and a distal end configured to expel analyte effluent;

an electrospray emitter coaxially disposed surrounding at least the distal end of the capillary, the electrospray emitter having a distal end that is tapered to terminate at an opening, the opening being coaxially disposed in relation to the distal end of the capillary; and a sheath liquid reservoir in liquid communication with an interior of the electrospray emitter, such that an electrically conductive sheath liquid is allowed to flow from the sheath liquid reservoir, through a connecting fixture intermediate the capillary and the electrospray emitter, across the distal end of the capillary, and through the opening at the distal end of the electrospray emitter;

wherein the sheath liquid provides electrical contact between the capillary and the electrospray emitter;

wherein the sheath-flow interface is configured to produce a nanospray generated by electrokinetic flow of the sheath liquid mixed with the analyte effluent; and wherein the electrokinetic flow is generated by an electric potential between the electrospray emitter and a target surface disposed adjacent, but not in physical contact with the opening of the emitter.

The interface disclosed herein is useful for producing electrospray from a capillary. It is known to those of skill in the art that electrospray can be used as the source of ions for mass spectrometry (MS), although it will be appreciated that the electrospray generated by the disclosed interface is not limited to use in tandem with MS, but can be used for any purpose requiring an electrospray.

Figure 1A:
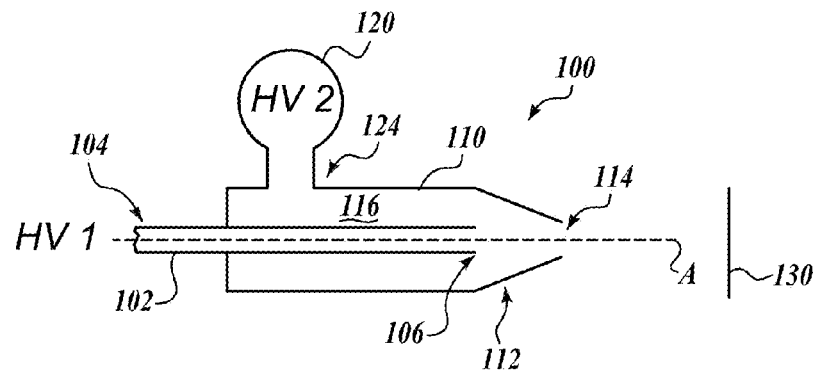
FIG. 1A. Schematic illustration of a representative interface in accordance with the disclosed embodiments.

The sheath-flow interface will now be described in greater detail with reference to FIG. 1A. The interface 100 includes a capillary 102. The capillary 102 includes an injection end 104 that is configured to receive an analyte liquid. The analyte liquid is introduced into the capillary 102 at the injection end 104 by any means known to those of skill in the art. For example, the injection end 104 can be interfaced with a chromatography column, such that effluent from the chromatography column is injected into the capillary 102. Other representative methods for providing analyte to the capillary 102 include contacting the injection end 104 with a reservoir of analyte and performing electrokinetic, hydrostatic or hydrodynamic injection.

The capillary 102 has a distal end 106 that is configured to expel analyte effluent. Analyte effluent is the term used to describe analyte that has passed through the length of the capillary 102 and is expelled from the distal end 106. In one embodiment, the analyte effluent is moved through the capillary 102 using an electrokinetic force (e.g., electroosmotic flow).

Disposed around the capillary 102 is an electrospray emitter 110. The electrospray emitter is coaxially disposed around at least the distal end 106 of the capillary 102, such that the capillary 102 and an opening 114 of the electrospray emitter 110 are coaxially arranged along axis A, as illustrated in FIG. 1A. A distal end 112 of the electrospray emitter 110 is tapered from the tubular cylindrical body of the emitter 110 in order to form the opening 114.

Electrospray is generated from the analyte effluent passing through the capillary 102 and through the opening 114 in the emitter 110. In order to produce the electrospray, a sheath liquid is provided, flowing through the interior 116 of the emitter 110. The sheath liquid is delivered to the interior 116 from a sheath liquid reservoir 120. A connecting fixture 124 provides the liquid communication between the sheath liquid reservoir 120 and the interior 116.

To provide the desired electrospray, the sheath liquid flows through the interior 116 of the emitter 110 past the distal end 106 of the capillary 102. When flowing past the distal end 106 of the capillary 102, the sheath liquid interacts with the analyte effluent expelled from the capillary 102 and forces the analyte effluent toward the opening 114. The electrospray generated includes a mixture of the analyte effluent and the sheath liquid.

The electrospray is generated by applying at least a voltage HV2 between the sheath liquid reservoir 120 and the target surface 130. The voltage HV2 drives electroosmotic flow of the sheath liquid, using the zeta potential at the emitter 110 surface. The HV2 voltage provides electrokinetic flow sufficient to generate an electrospray from the opening 114. The target surface 130 can be held at ground or at a voltage.

In embodiments where a voltage HV1 is applied to the capillary 102, the electrospray is maintained by the electric field at the emitter opening 114, which is generated by a combination of voltage HV1 and HV2, or a surface potential at the target surface 130. In such an arrangement, both HV1 and HV2 potentials contribute to the electric field at the emitter. The HV1 potential is required in certain embodiments due to the large voltage drop across a narrow separation capillary in certain cases, which may be insufficient to maintain electrospray. The HV2 voltage or the surface potential at the target surface 130 are additional sources of potential that can be regulated to maintain desired electric field at the emitter.

In certain embodiments, the electrospray is a nanospray. As used herein, the term "nanospray" refers to a method of creating an aerosol of sub-micrometer-sized droplets. It is a form of electrospray ionization in which the electrostatic field overcomes the surface tension of a liquid to form a liquid jet. Nanospray employs glass capillaries with micrometer-sized exits and flow rates in the nL/minute range.

In certain embodiments, the capillary 102 is used for capillary electrophoresis (CE). When the interface is configured for CE, the voltage dropped across HV1 to HV2 provides electrokinetic flow in the form of electrokinetic separation for the analyte passing through the capillary 102.

The sheath liquid has electrical conductivity properties such that an electrical connection sufficient to drive the electrospray generating process is provided between the distal end 106 of the capillary 102 and the distal end 112 of the emitter 110.

The current generated by electrospray is proportional to the conductivity of the liquid. The representative sheath liquids include 10 mM formic acid or acetic acid in 50% methanol/acetonitrile or isopropanol. Percentage of organic solvents can vary. Volatile salts, such as ammonium formate or ammonium acetate can also be added to sheath liquid.

The analyte can be any composition of matter borne by the analyte liquid through the capillary 102. The analyte may be the analyte liquid itself; the analyte may be dissolved within the analyte liquid; the analyte may be heterogeneously mixed with the analyte liquid; or combinations thereof. Representative analytes include polar small molecules and large biomolecules (e.g., metabolites, peptides, proteins, lipids, glycans, and nucleic acids). Other representative analytes include pesticides, environmental contaminants, and pharmaceuticals and their contaminants, metabolites, etc.

The individual components of the interface 100 will now be described in greater detail.

The capillary 102 can be any capillary known to those of skill in the art. Representative capillaries are formed from glass (e.g., fused silica) or plastic and are cylindrical bodies having a tubular form wherein the inner diameter of the capillary is on the order of from 0.5 microns to 500 microns in diameter. In one embodiment, the inner diameter is from 5 to 75 microns.

The emitter 110 can be formed from glass, fused silica, and any other materials known to those of skill in the art. Polymers, such as TEFLON, can also be used, as can ceramics and any non-conductive material that can be shaped to form the appropriate structure of the emitter 110 as described herein. The emitter 110 is typically a uniform cylinder prior to the taper towards the distal end 112. However, the emitter 110 can also be tapered throughout, or have a non-circular cross section.

The inner diameter of the emitter 110 must be larger than the outer diameter of the capillary 102, so as to allow the capillary to fit inside. The interior 116 of the emitter 110 is defined by the space between the outer surface of the capillary 102 and the inner surface of the emitter 110.

The opening 114 of the emitter 110 partially defines the shape and size of the electrospray generated. In one embodiment, the opening 114 in the distal end of the electrospray emitter is from 0.5 to 30 microns in diameter. The opening 114 is typically circular, although in certain embodiments the opening is non-circular.

In one embodiment, the distal end of the capillary and the electrospray emitter are separated by a distance of at least 0.1 mm. The distance between the distal end of the capillary and the emitter affects the electrical communication throughout the interface. This is particularly true if the capillary is used for CE, through the application of HV1.

Figure 2:
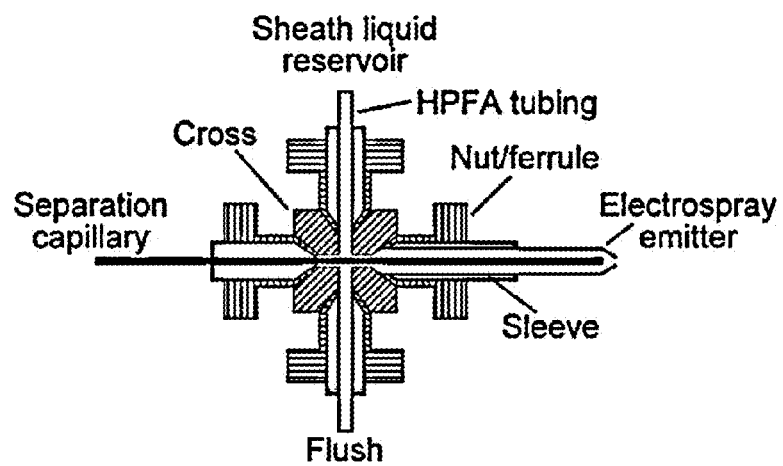
FIG. 2. Components used in the construction of an exemplary interface.

Valves, tubing, and other fluidic control components can be used as the connecting fixture 124. An example of a representative connecting fixture 124 is illustrated in FIG. 2. The connecting fixture 124 can be made of TEFLON or other polymer tubing, glass, or fused silica. A switching valve (not pictured) can be incorporated to switch between multiple sheath fluids (i.e., between multiple sheath liquid reservoirs, if desired. The dimensions of the connecting fixture 124 are tied to the dimensions of the capillary 102 and the emitter 110. Representative inner diameters are from 10 microns to five mm and a length of from one mm to 30 cm.

Electrical potential drives the operation of the interface 100. In the most basic embodiment, the application of a potential, HV2, at the sheath liquid reservoir 120, with a ground or counter potential at the target surface 130. HV2 can be applied to the sheath liquid reservoir 120 in a number of ways, such as by electrical contact to an electrode disposed in the sheath liquid reservoir 120. For example, a wire electrode can be submerged in the sheath liquid reservoir 120 or an electrode can be disposed on a wall of the sheath liquid reservoir 120.

In one embodiment, the analyte liquid is moved through the capillary by a force selected from the group consisting of an electrokinetic force and a mechanical pumping force. Electrokinetic forces are well known to those of skill in the art and include, but are not limited to, dielectrophoresis, and electroosmotic flow.

In embodiments where electrokinetic flow is used, the optional voltage HV1 is used. HV1 can be applied by making electrical contact to the analyte liquid. For example, an electrode may be disposed at the injection end 104 of the capillary 102, or a wire electrode can be used to contact the analyte liquid near the injection end 104.

In one embodiment, the analyte liquid is separated within the capillary by a technique selected from the group consisting of capillary zone electrophoresis, micellar electrokinetic chromatography, capillary electrochromatography, dielectrophoresis, and combinations thereof.

In one embodiment, the analyte liquid is separated by liquid chromatography prior to entering the injection end of the capillary. The analyte liquid need not always be separated when traveling through the capillary. Instead, the capillary may receive pre-separated effluent and simply transport the analyte in order to generate the electrospray. Any chromatographic technique can be used to provide the analyte liquid to the capillary, as long as the effluent of the chromatographic process can be provided and interfaced with the injection end of the capillary.

In one embodiment, the analyte liquid is separated within the capillary by electrophoresis, wherein the nanospray is produced by electroosmotic flow, and wherein both the electrophoresis and the electroosmotic flow are driven by applying an electric potential between the injection end of the capillary, the sheath liquid reservoir, and the target surface.

In one embodiment, the sheath-flow interface 100 is configured to provide the nanospray to a mass spectrometer for analysis. In this embodiment, the target surface 130 is an input orifice of the mass spectrometer. Such a configuration is explicitly illustrated in FIG. 1B and described in greater detail in the Example 1 below.

When the interface 100 is used for mass spectrometry, the sheath liquid can be configured to enhance the compatibility of the analyte effluent with the mass spectrometer. Particularly, if analyte effluent is not by itself compatible with MS, the sheath liquid can be selected so as to facilitate effective MS. For example, if CE is used to provide the analyte effluent, some common buffers are not compatible with MS, but if a proper sheath liquid is used, the buffer and analyte contained therein can be analyzed by MS.

In another aspect, methods are provided for producing a nanospray of an analyte effluent from a capillary using a sheath-flow interface as disclosed herein. In one embodiment the method comprises the step of applying a voltage to the sheath liquid reservoir sufficient to drive electroosmotic flow of the sheath liquid from the sheath liquid reservoir, through a connecting fixture intermediate the capillary and the electrospray emitter, across the distal end of the capillary, and through the opening at the distal end of the electrospray emitter.

In one embodiment the analyte effluent is separated within the capillary by capillary electrophoresis by applying a voltage to the injection end of the capillary.

However, in other embodiments, the analyte effluent is separated by liquid chromatography (or other separation method) prior to entering the capillary. Furthermore, in other embodiments the analyte effluent is not separated either before entering or while traveling through the capillary.

As described above, the interface can be used as an ionization source for mass spectrometry. Accordingly, in certain embodiments of the method, the electrospray is ionized and directed into an input orifice of a mass spectrometer for analysis.

The following examples are included for the purpose of illustrating, not limiting, the embodiments disclosed herein.

EXAMPLES

Example 1

Design and Testing of CE-MS Nanospray Interface

In the present study, we report a simplified version of a nanospray sheath flow interface, in which a stable spray is achieved with very low sheath flow rates and without a pump or nebulizer gas. In our design, the separation capillary is placed inside a tapered glass emitter. Sheath liquid is driven by electroosmosis, produced by the zeta potential at the emitter surface. This liquid flows over the end of separation capillary, closing the circuit and mixing with the capillary effluent inside the tip. The capillary, the electrospray emitter, and sheath liquid tubing are connected via a PEEK cross. The small emitter tip size (2 to 10 µm i.d.) allows for operation in the nanospray regime.

In a typical interface design, electrospray voltage is applied directly to the electrospray tip, which often requires the use of metal or metal-coated emitters or a wire electrode inside an emitter. However, the lifetime of a metal-coated emitter is limited. Although metal emitters are sturdier than glass, redox reactions on the metal surface often lead to bubble formation and corona discharge, which limits the electrospray. Wire electrodes also have their limitations—they can create turbulent flow and loss of separation efficiency. Alternatively, carbon-coated and conductive polymer coated capillaries have been used to supply current to the tip. Unfortunately, carbon coatings have limited lifespan and must be periodically replaced. Conductive polymers must be applied to the exterior of the emitter, which can require care to avoid blockage. We circumvent these problems by applying voltage to the tip indirectly—via a platinum electrode placed in a sheath buffer reservoir.

Experimental

Materials and Reagents

All reagents were purchased from Sigma Aldrich Co, St. Louis, Mo., unless otherwise noted. Peptide standards were purchased from Anaspec, Inc., San Jose, Calif. Borosilicate capillaries for electrospray emitters were purchased from Sutter Instrument Co., Novato, Calif. Fused silica separation capillaries were purchased from Polymicro Technologies, Phoenix, Ariz., USA. PEEK cross, nuts, ferrules, sleeves and PHFA tubing were purchased from Idex Health and Science, Oak Harbor, Wash.

Interface

Figure 1B:
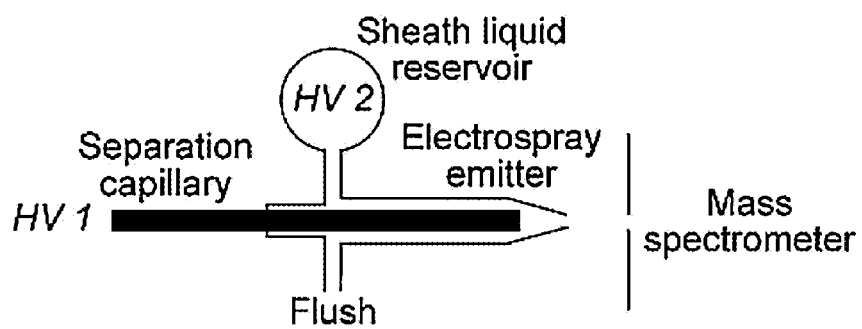
FIG. 1B. Schematic of a representative interface with a mass spectrometer. The sheath liquid is pumped by electrokinetic flow driven by the potential difference between HV2 and an inlet of the mass spectrometer. The separation is driven by the potential difference between the inlet (HV1) and outlet (HV2) of the capillary.

A schematic of the interface is shown in FIG. 1B. The separation capillary was threaded into a glass electrospray emitter using a cross fitting (5-mm-long cross channels with 0.5 mm i.d.). One arm of the cross was fitted with HPFA tubing (0.5 mm i.d.) that was dipped into a microcentrifuge tube, which acted as the sheath liquid reservoir. The height of the liquid in the reservoir was kept at the same height as the emitter tip to avoid hydrodynamic flow. High voltage was applied to the injection end of the capillary (HV 1) and to the sheath liquid reservoir (HV 2); the separation was driven by the difference in these potentials. HV 2 provided the potential that drives electro-osmotic flow in the emitter. The mass spectrometer inlet was held at ground potential. The other arm of the cross was used to flush the interface with sheath fluid at the start of an experiment.

Electrospray emitters were pulled from 10 cm long borosilicate glass capillaries (1 mm o.d., 0.75 mm i.d.) with a P-97 Sutter Puller. The tip sizes used in the experiments ranged from 2 to 10 µm i.d. with the taper length of about 3 mm. The tip diameter was estimated by inspection of the tip under a microscope. The outer diameter of the tip was noted, and the inner diameter was estimated based on the ratio of the inner to outer diameter of the starting glass capillary.

A detailed drawing of the interface is presented in FIG. 2. A fused silica separation capillary (50 µm i.d., 150 um o.d., 45 cm long) was threaded through a PEEK coned port cross (Upchurch). The capillary was threaded into the electrospray emitter. The capillary and emitter tip were held in place with a sleeve, ferrule, and matching nut. The distance from the capillary tip to the emitter tip was adjusted while viewing the system under a microscope as the fittings were tightened. Sheath liquid was introduced into the electrospray tip via an HPFA tubing connected to the cross. The fourth port of the cross was connected to a syringe and used to flush the interface with sheath liquid at the start of an experiment.

Voltage was delivered from power supplies (Spellman CZE 1000R) via platinum electrodes that were in contact with the running buffer and to the sheath liquid reservoir. The cross was attached to a translation stage placed at the source of Thermo LCQ ion trap instrument.

CE-MS

All CE-MS experiments were performed with a Thermo Finnigan LCQ ion trap instrument. Samples were 50 µM human angiotensin II, phosphorylated angiotensin II, and insulin receptor. Capillaries were conditioned with 0.1 M HCl, followed by 1 M NaOH, and then separation buffer, all injected under 1 psi pressure for 5 minutes before use.

In continuous infusion experiments, the sample was electrokinetically introduced into the separation capillary. Continuous infusion was used to tune the instrument for the optimal peptide signal. For capillary electrophoresis analysis, samples were electrokinetically injected. In all experiments, the emitter tip was placed 2 mm away from the ion source. The optimal tuning parameters included lens voltage of −38 V and capillary temperature of 165° C.

In positive ion mode experiments, the separation buffer was 10 mm ammonium acetate, pH 7.8, and the sheath liquid was an equal volume mixture of 10 mm aqueous acetic acid and methanol.

In negative ion mode experiments, Ultratrol LN (Target Discovery, TM) coating was applied to the capillary to minimize electroosmotic flow. The separation buffer consisted of 10 mm ammonium acetate, pH 8, and the sheath liquid was an equal volume mixture of 10 mm aqueous ammonium acetate and methanol.

Numerical Modeling

To understand the electrokinetic transport process in the interface, numerical modeling of species transport inside the interface was carried out with commercial software based on finite element analysis (Comsol Mulitphysics Software 3.5). The solution was used to estimate flow rate, electric field, and sample concentration in the region between the capillary exit and electrospray tip. This modeling did not consider nanospray formation at the electrospray tip in order to minimize complexity in the calculation.

The modeling procedure with Comsol involves creating geometry, meshing the geometry, defining subdomain and boundary physics, solving the solution, and postprocessing. In our case, a simplified 2D geometric model represents the 0.6 cm segment of the electrospray tip (including separation capillary) placed 1 mm away from the ion source. The emitter was assumed to be a cone with a taper length of 3 mm and the tip i.d. of 5 µm.

The model couples three physical phenomena:
1. Generalized Maxwell equation to solve for electric potential and field strength, $$-\nabla \cdot (\sigma \nabla V) = Q \quad (1)$$

For Eq. 1, a Dirichlet boundary condition at the capillary inlets is specified and potential of 0 V applied at the boundary representing the MS source.

2. Navier-Stokes equation to calculate electroosmotic flow velocity under the applied voltage, $$\rho(u \cdot \nabla)u = \nabla \cdot [-pI + \eta(\nabla u + (\nabla u)^T)] \quad (2)$$

with a Dirichlet boundary condition ($u = u_{eo} = E$) defined at the walls of separation capillary and the electrospray interface walls, and a Neumann condition at the inlet of the separation capillary and electrospray interface. A continuity boundary condition is maintained at the electro spray tip exit.

3. The mass conservation equation was solved for electroosmotic flow driven species transport.

$$\partial c/\partial t + \nabla \cdot (-D\nabla c) = R + u \cdot \nabla c \quad (3)$$

with Dirichlet boundary condition at the capillary inlet and convective flux condition at the electrospray tip outlet. Continuity condition is maintained at the separation capillary exit. The reaction term, R, is zero in this case.

In these equations, $\sigma$ ($Sm^{-1}$) is conductivity, V (V) is the electric potential, Q ($Am^{-3}$) is the current source, $\rho$ ($kgm^{-3}$) is density, p (Pa) is pressure, $\eta$ (Pa·s) is dynamic viscosity, u ($ms^{-1}$) is velocity, $u_{eo}$ ($m^2s^{-1}V^{-1}$) is electroosmotic mobility, E (V/m) is electric field, c ($molm^{-3}$) is species concentration, and D ($m^2s^{-1}$) is diffusivity. D is estimated according to the Nernst equation as $D = RTu_{eo}/F$, where R is gas constant, T (K) is temperature, and F is Faraday constant. Equation 1, 2, and 3 were solved simultaneously to obtain solutions for potential (V), electroosmotic flow driven velocity (u), and species concentration ($c_i$). It is assumed that the electroosmotic mobility for both separation buffer and sheath liquid is the same and equals $4.2 \times 10^{-8}$ $m^2/(V*s)$. That value was measured experimentally with neutral electroosmotic flow marker rhodamine B in 10 mm ammonium acetate, pH 8. Equal conductivity for separation buffer and sheath liquid was assumed to be 1 mS/cm. With equal electroosmotic flow, the ratio of the electric potential of separation buffer and sheath liquid is proportional to the ratio of the separation buffer and sheath liquid flow rates.

Results and Discussion

Numerical Modeling:

Modeling allowed us to examine the effect of different parameters that can affect signal at the emitter, such as different tip sizes, buffer viscosity, relative conductivity of the separation buffer and sheath liquid, and the distance between capillary and emitter exits. Among those, the voltage program and the distance from the capillary exit to the emitter exit significantly affect the performance of the ESI emitter.

The electric potential at the tip is controlled by potentials applied at the capillary exit and sheath liquid reservoir. The value of electric field strength at the emitter tip calculated with the model was $5*10^6$ V/m. This value, which falls within range of values reported in the literature, assumes 1 kV sheath liquid potential (70 V/cm), 200 V/cm separation field, 5-1 µm tip diameter, and 1 mm distance between the capillary and emitter exits.

Figure 3:
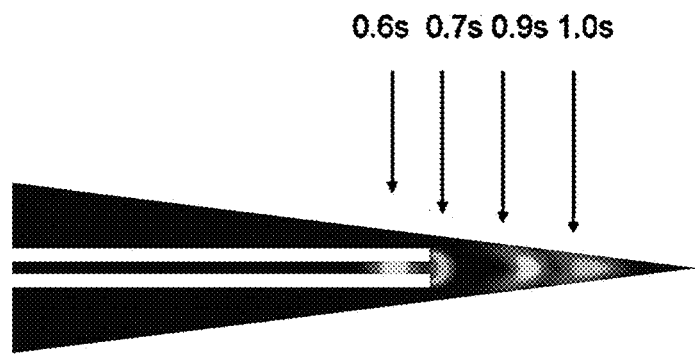
FIG. 3. Sample plug concentration profile at different time points, in the region between capillary exit and electrospray ionization (ESI) emitter. Separation buffer potential: 250V/cm, sheath liquid potential: 100V/cm.

Different voltage combinations will also result in different flow profile inside the emitter. FIG. 3 shows the transient profile of sample plug as it transits from separation capillary through the emitter. The sample plugs in the emitter reveal possible source of tailing in the signal due to relatively slow flow profile at the edges. However, this broadening can be minimized by adjusting the separation and sheath voltages.

Figure 4:
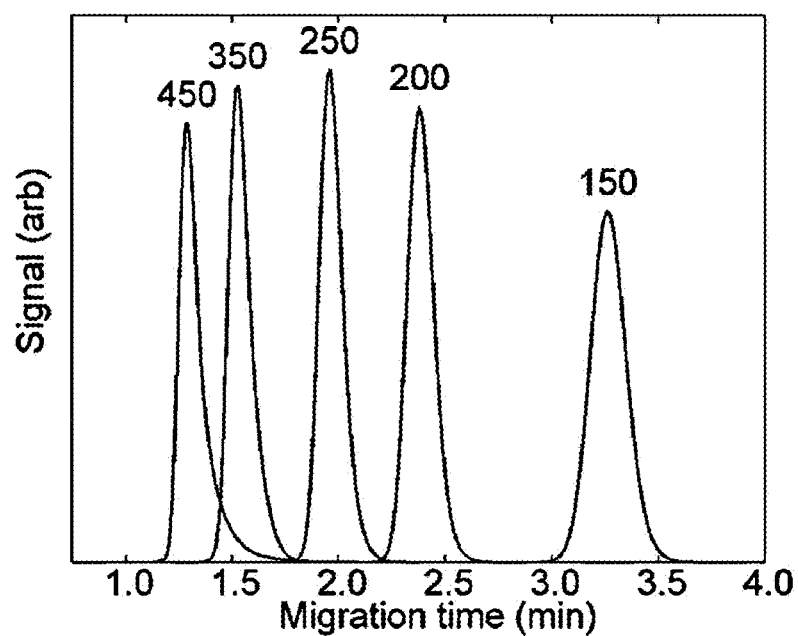
FIG. 4. Sample plug concentration profiles integrated at the ESI emitter exit boundary. Sheath liquid potential: 100 V/cm, capillary potential: 150 to 450 V/cm. The numbers above the peaks are the electric fields used for the separations in V/cm.

FIG. 4 shows transient concentration profile, obtained as boundary integration of $c_i$ for the sample at the emitter exit, for a sheath liquid potential of 100 V/cm and separation potentials of 150 to 450 V/cm, which are typically used in CE separations. Based on FIG. 4, it is apparent that there is an optimal voltage program for separation buffer/sheath liquid flow rate ratios that minimizes tailing and extracolumn band broadening.

At high ratios of separation potential to sheath liquid potential, radial diffusion of the sample plug is enhanced in the region between the capillary exit and the emitter tip and a tendency is observed for sample to flow toward the sheath liquid inlet, which results in peak tailing and lower resolution. The model shows that this effect can be minimized with lowered sheath liquid conductivity (data not shown). In the lower range of separation electric fields, performance degrades predominantly due to lowered separation voltage.

Figure 5A:
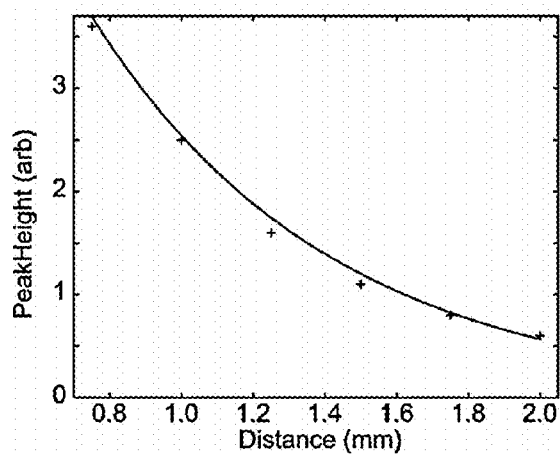
FIGS. 5A-5C. Comsol model of effects of distance between capillary and emitter on peak height, width, and asymmetry factor. Sample plug concentration profiles were integrated at the ESI emitter exit boundary processed with in-house software, SigMan 1.2.0. A least-squares fit of an exponential to the data is shown in A; least squares fit of a line to the data is shown in 5B and 5C. Data are for an electric field of 450 V/cm applied to the separation capillary and 100 V/cm applied to the emitter (plus signs and solid curves), except for panel C, which also includes data for an electric field of 300 V/cm applied to the separation capillary and 100 V/cm applied to the emitter (circles and dashed line).
Figure 5B:
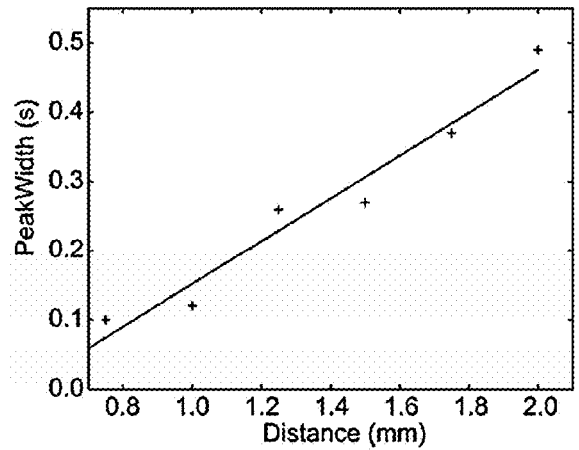

Another important factor is the distance between the capillary exit and the emitter tip. FIG. 5 illustrates effect of the capillary-to-tip distance on peak height, peak width, and asymmetry factor (calculated at 10% of peak height). Peak height decreases exponentially with distance from the capillary exit to the emitter tip (FIG. 5A). Peak width and asymmetry increase linearly with distance (FIGS. 5B and C).

Figure 5C:
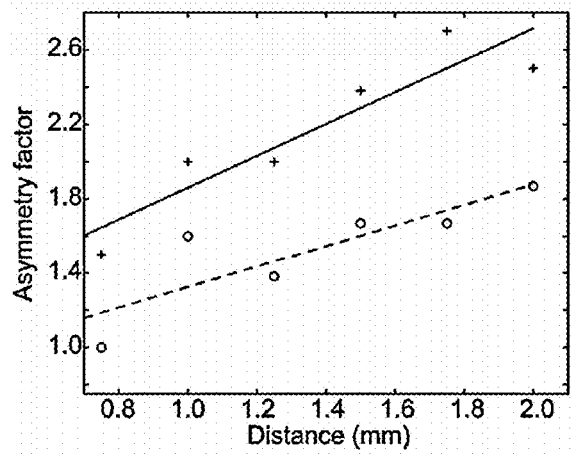

The results were obtained with an electric field of 450 V/cm applied to the separation capillary and 100 V/cm applied to the emitter. Essentially identical results were obtained for the peak height and width when an electric field of 300 V/cm was applied to the separation capillary and 100 V/cm applied to the emitter (data not shown). However, the asymmetry factor decreased dramatically when the electric field strength on the separation capillary was decreased to 300 V/cm (FIG. 5C).

Experimental Evaluation

Flow Rate and Electrospray Voltage

Voltage and flow rate are important parameters affecting electrospray stability and signal. In our interface, the electrospray voltage is affected by both the separation voltage and the voltage applied to sheath liquid reservoir. The sheath flow rate is driven by electroosmotic flow in the emitter.

A solution of 50 µM angiotensin II was continuously infused while electrospray and electrophoresis voltages were varied. While electrospray could be initiated with the separation voltage alone, applying 1 kV voltage to the sheath liquid buffer provided the best signal-to-noise ratio for the peptide standard under a wide range of separation electric fields (150 to 350 V/cm).

Distance Between Capillary Exit and the Emitter Tip

Our numerical model showed the distance between the capillary tip and the emitter tip also affects interface performance. Although minimizing this distance will also minimize dead volume, larger distances may provide better mixing of the sample with sheath liquid buffer, which may improve ionization efficiency.

Figure 6:
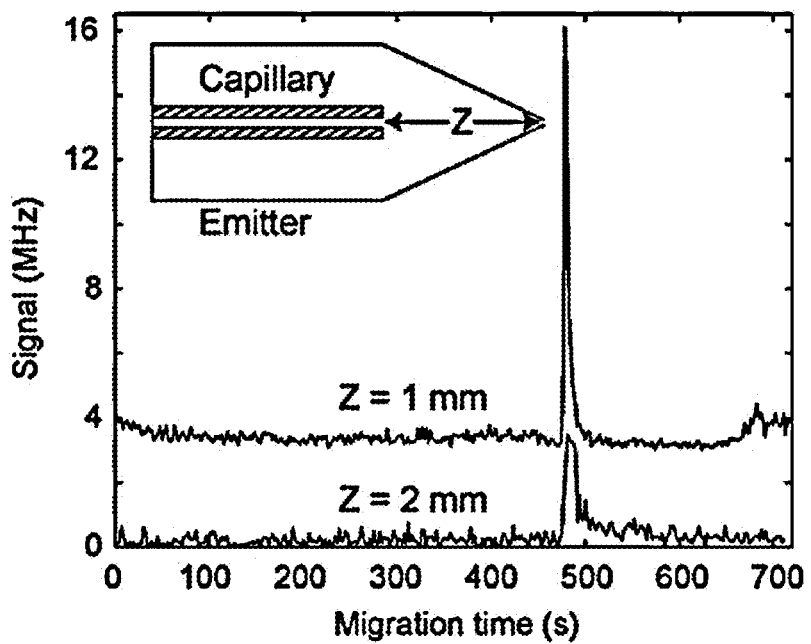
FIG. 6. Extracted ion electropherogram of doubly charged angiotensin II (m/z 524.3) generated with capillary exit spaced 1 mm (top trace) and 2 mm from the electrospray emitter (bottom trace). 50 µM angiotensin II, injection: 9 kV for 2 sec. 250V/cm separation (12,500 V applied to injection end, 1,000 V applied to emitter). The tip was 10 µm in diameter.

The effect of capillary-to-emitter tip distance was evaluated by performing a capillary electrophoresis analysis of a 50 µM solution of angiotensin II using a 10 µm i.d. emitter and 50 µm i.d. capillary, FIG. 3. The distance between the end of the separation capillary and the tip of the emitter was adjusted to 1-mm and 2-mm, FIG. 6. Peak area was estimated by summing the counts across the peak and subtracting the counts from the background. A nonlinear least-squares routine was used to fit a Gaussian function to the peaks; the resulting peak standard deviation was used to determine the plate counts. Finally, noise was determined as the standard deviation of a 60-s segment of the background before the peak appeared.

The 2-mm spacing produced a much broader and lower amplitude peak. The peak areas for the two electropherograms differ by only 10%. No sample is lost in the interface; the decrease in peak height is solely due to extracolumn band broadening. The 1-mm spacing produced a three-fold higher peak, a five-fold higher signal-to-noise ratio, and a ten-fold higher plate count than the 2-mm spacing. Clearly, the shorter spacing between the tip of the separation capillary and the tip of the emitter results in much less extracolumn band broadening. The experimental results are in agreement with the model, which predicted a source of peak tailing due to the high ratio of the separation voltage to sheath voltage used in the experiment.

Tip Size

Figure 7:
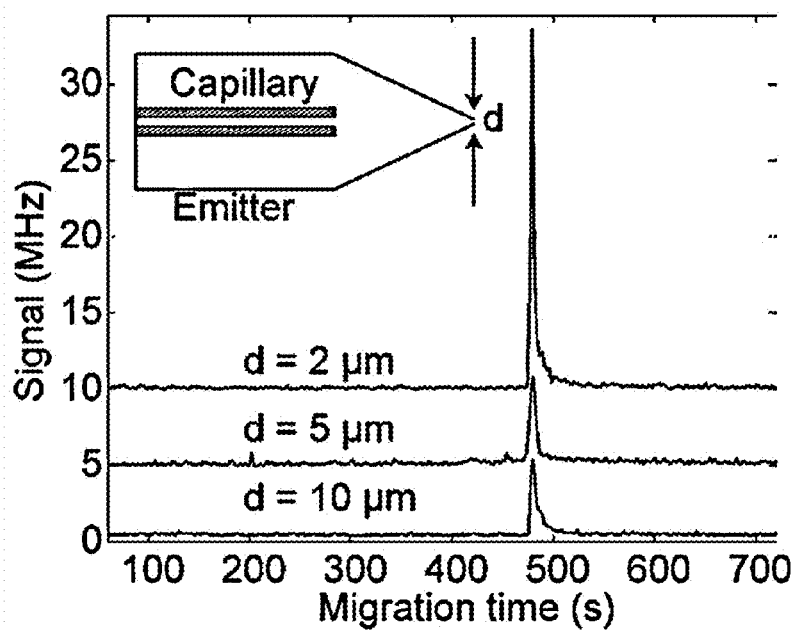
FIG. 7. Extracted ion electropherograms of angiotensin II, generated with 3 tip sizes. Injection: 9 kV for 2 sec, 300V/cm separation (14,500 V applied to injection end, 1,000 V applied to emitter).

We investigated the effect of tip size on the electrospray efficiency, FIG. 7. All tip sizes produced a stable spray with separation field strength up to 350 V/cm. Table 1 summarizes the performance of the three tips. The 5-µm and 10-µm diameter tips produced similar signal amplitude. In contrast, the 2-µm tip produced a much higher signal and signal-to-noise ratio, which suggests that electrospray was much more efficient from the small diameter tip.

TABLE 1

Effect of tip size on capillary electrophoresis-electrospray performance (data from FIG. 7).

| Tip Diameter | Plate count (m/z = 524) | Peak Area | Signal-to-noise | Detection limit (fmol) |
|---|---|---|---|---|
| 2 | 90,000 | $6.4 \times 10^7$ | 350 | 1 |
| 5 | 25,000 | $2.6 \times 10^7$ | 50 | 10 |
| 10 | 30,000 | $2.5 \times 10^7$ | 50 | 10 |

Figure 8:
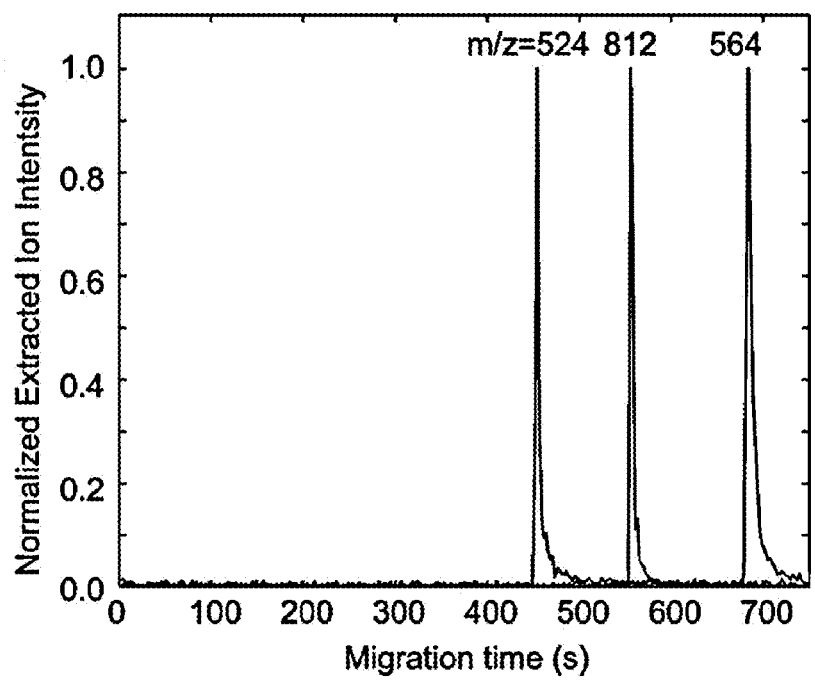
FIG. 8. Extracted ion electropherograms of angiotensin II (m/z=524), phosphorylated angiotensin II (m/z=564), and insulin receptor fragment 1142-1153 (m/z=812), generated with a 2-µm diameter tip. Injection: 9 kV for 2 sec, 300V/cm separation (14,500 V applied to injection end, 1,000 V applied to emitter).

The sample used for the 2-µm diameter tip also included phosphorylated angiotensin II and insulin receptor. FIG. 8 presents the reconstructed electropherogram for these three peptides. The peaks were reasonably sharp with only a modest amount of tailing. A nonlinear least-squares routine was used to fit a Gaussian function to the peaks. Table 2 summarizes the results of the analysis. Phosphorylated angiotensin II generated better signal-to-noise ratio and detection limits, but poorer separation efficiency, than angiotensin II. Insulin receptor generated much better separation efficiency and detection limits than the other peptides; the plate count for this peak was 220,000 and the detection limit was 100 amol injected onto the capillary.

TABLE 2

Capillary electrophoresis/electrospray ionization for the separation of three peptides (data from FIG. 8).

| Peptide m/z | Plate count | Signal-to-noise | Detection limit (fmol) |
|---|---|---|---|
| 524 | 90,000 | 350 | 1 |
| 564 | 56,000 | 2,000 | 0.2 |
| 812 | 220,000 | 3,500 | 0.1 |

Spray Stability

Figure 9:
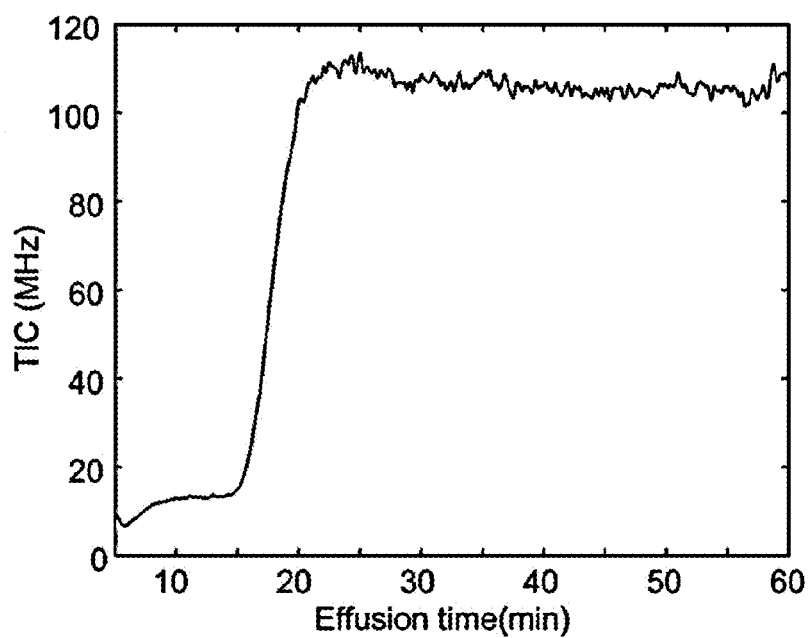
FIG. 9. Infusion of a 50-µM solution of angiotensin II. The first five minutes are not shown.

The spray stability was evaluated by continuous injection of a 50 µM solution of angiotensin II, FIG. 9. The peptide appeared at the detector after ~20 minutes, and generated a relatively stable signal, with no dropouts observed. The relative standard deviation in the total ion count was 2% from 20 to 60 minutes. The relative standard deviation at the extracted ion count was slightly poorer, 3%, across this same interval.

Low Flow, Negative Ion Conditions

Figure 10:
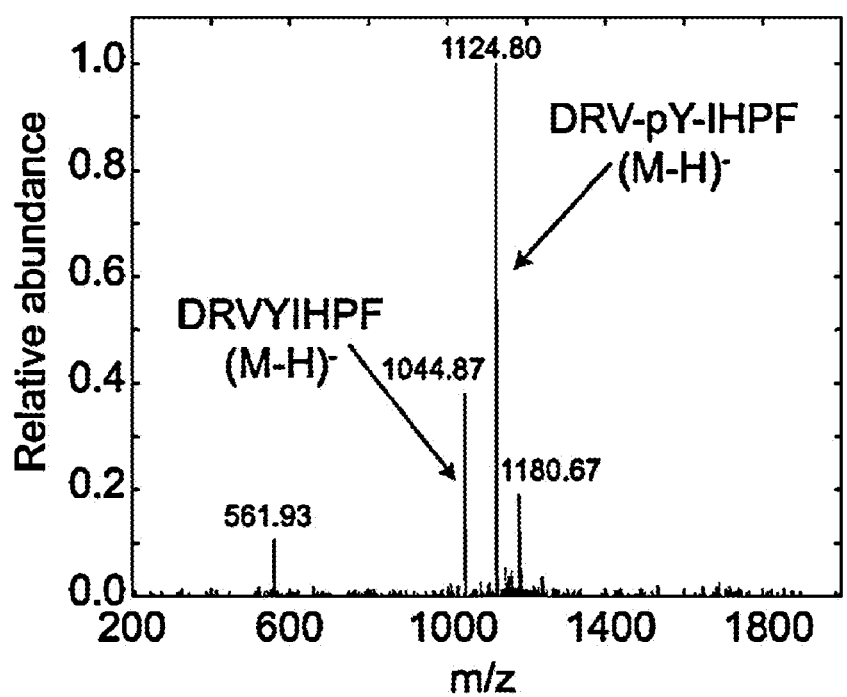
FIG. 10. The 5-second averaged spectrum of 50 µM mixture of phosphorylated and non-phosphorylated angiotensin II, detected in negative ion mode. The mixture was continuously injected at a field strength of −250 V/cm. A voltage of −1 kV was applied to sheath liquid buffer. Tip size was 5 µm i.d. and 50 um capillary exit was positioned 1 mm away from the emitter tip.

To evaluate the interface performance under low flow conditions, we used a capillary coated with Ultratrol LN to infuse a mixture of phosphorylated and non-phosphorylated angiotensin II into the interface. FIG. 10 presents the spectrum of a continuously infused peptide mixture, detected in negative ion mode and averaged for five seconds.

While illustrative embodiments have been illustrated and described, it will be appreciated that various changes can be made therein without departing from the spirit and scope of the invention.

The invention claimed is:

1. A sheath-flow interface for producing electrospray from a capillary, comprising:

a capillary configured to contain an analyte liquid, the capillary having an injection end configured to receive the analyte liquid and a distal end configured to expel analyte effluent;

an electrospray emitter coaxially disposed surrounding and extending longitudinally beyond the distal end of the capillary, the electrospray emitter having a distal end that is tapered to terminate at an opening, the opening being coaxially disposed in relation to the distal end of the capillary, the electrospray emitter also having an emitter interior defining a fluid channel within the electrospray emitter and surrounding the capillary such that the distal end of the capillary is disposed within the fluid channel; and a sheath liquid reservoir in liquid communication with the emitter interior of the electrospray emitter through a connecting fixture, wherein the sheath liquid reservoir comprises a first electrode configured to drive electroosmotic flow of an electrically conductive sheath liquid from the sheath liquid reservoir, through the connecting fixture, into the emitter interior, across the distal end of the capillary where it entrains the analyte liquid prior to exiting through the opening at the distal end of the electrospray emitter;

wherein the sheath liquid provides electrical contact between the capillary and the electrospray emitter;

wherein the sheath-flow interface is configured to produce a nanospray generated by electrokinetic flow of the sheath liquid mixed with the analyte effluent; and wherein the electrokinetic flow is generated by an electric potential between the electrospray emitter and a target surface disposed adjacent, but not in physical contact with, the opening of the emitter.

2. The sheath-flow interface of claim 1, wherein the analyte liquid is moved through the capillary by a force selected from the group consisting of an electrokinetic force and a mechanical pumping force.

3. The sheath-flow interface of claim 1, wherein the analyte liquid is separated within the capillary by a technique selected from the group consisting of capillary zone electrophoresis, micellar electrokinetic chromatography, capillary electrochromatography, capillary isoelectrofocusing, and combinations thereof.

4. The sheath-flow interface of claim 1, wherein the analyte liquid is separated by liquid chromatography prior to entering the injection end of the capillary.

5. The sheath-flow interface of claim 1, wherein the nanospray is produced by electroosmotic flow.

6. The sheath-flow interface of claim 1, wherein the analyte liquid is separated within the capillary by electrophoresis, wherein the nanospray is produced by electroosmotic flow, and wherein both the electrophoresis and the electroosmotic flow are driven by applying an electric potential between the injection end of the capillary, the sheath liquid reservoir, and the target surface.

7. The sheath-flow interface of claim 1, wherein the sheath-flow interface is configured to provide the nanospray to a mass spectrometer for analysis, and wherein the target surface is an input orifice of the mass spectrometer.

8. The sheath-flow interface of claim 7, wherein the sheath liquid is configured to enhance the compatibility of the analyte effluent with the mass spectrometer.

9. The sheath-flow interface of claim 1, wherein the distal end of the capillary and the electrospray emitter are separated by a distance of at least 0.1 mm.

10. The sheath-flow interface of claim 1, wherein the opening in the distal end of the electrospray emitter is from 0.5 to 30 microns in diameter.

11. The sheath-flow interface of claim 1, wherein the target surface is held at ground.

12. The sheath-flow interface of claim 1, wherein the target surface is held at a potential.

13. The sheath-flow interface of claim 1, wherein the opening in the distal end of the electrospray emitter is from 0.5 to 10 microns in diameter.

14. A method for producing a nanospray of an analyte effluent from a capillary using a sheath-flow interface according to claim 1, comprising applying a voltage to the sheath liquid reservoir sufficient to drive electroosmotic flow of the sheath liquid from the sheath liquid reservoir, through a connecting fixture intermediate the capillary and the electrospray emitter, across the distal end of the capillary, and through the opening at the distal end of the electrospray emitter.

15. The method of claim 14, wherein the analyte effluent is separated within the capillary by capillary electrophoresis by applying a voltage to the injection end of the capillary.

16. The method of claim 14, wherein the analyte effluent is separated by liquid chromatography.

17. The method of claim 14, wherein the analyte effluent is not separated.

18. A sheath-flow interface for producing electrospray from a capillary, comprising:

a capillary configured to contain an analyte liquid, the capillary having an injection end configured to receive the analyte liquid and a distal end configured to expel analyte effluent;

an electrospray emitter coaxially disposed surrounding and extending longitudinally beyond the distal end of the capillary, the electrospray emitter having a distal end that is tapered to terminate at an opening, the opening being coaxially disposed in relation to the distal end of the capillary, the electrospray emitter also having an emitter interior defining a fluid channel within the electrospray emitter and surrounding the capillary such that the distal end of the capillary is disposed within the fluid channel; and a sheath liquid reservoir in liquid communication with an interior of the electrospray emitter through a connecting fixture, such that an electrically conductive sheath liquid is allowed to flow from the sheath liquid reservoir, through the connecting fixture, into the emitter interior, across the distal end of the capillary where it entrains the analyte liquid prior to exiting through the opening at the distal end of the electrospray emitter;

wherein the connecting fixture provides liquid communication between a second liquid source and the interior of the emitter, in addition to the sheath liquid reservoir;

wherein the sheath liquid provides electrical contact between the capillary and the electrospray emitter;

wherein the sheath-flow interface is configured to produce a nanospray generated by electrokinetic flow of the sheath liquid mixed with the analyte effluent; and wherein the electrokinetic flow is generated by an electric potential between the electrospray emitter and a target surface disposed adjacent, but not in physical contact with, the opening of the emitter.

19. The sheath-flow interface of claim 18, wherein the second liquid source is a second source of sheath liquid.

* * * * *